(12) United States Patent
Fukuda et al.

(10) Patent No.: US 10,952,517 B2
(45) Date of Patent: Mar. 23, 2021

(54) COAT-FORMING DEVICE

(71) Applicant: KAO CORPORATION, Tokyo (JP)

(72) Inventors: Ikuo Fukuda, Chikusei (JP); Shinji Kodama, Chiba (JP)

(73) Assignee: KAO CORPORATION, Tokyo (JP)

( * ) Notice: Subject to any disclaimer, the term of this patent is extended or adjusted under 35 U.S.C. 154(b) by 21 days.

(21) Appl. No.: 15/775,997

(22) PCT Filed: Nov. 4, 2016

(86) PCT No.: PCT/JP2016/082877
§ 371 (c)(1),
(2) Date: May 14, 2018

(87) PCT Pub. No.: WO2017/082179
PCT Pub. Date: May 18, 2017

(65) Prior Publication Data
US 2018/0317627 A1    Nov. 8, 2018

(30) Foreign Application Priority Data

Nov. 12, 2015  (JP) .............................. JP2015-222336

(51) Int. Cl.
*A45D 34/04* (2006.01)
*A61K 8/04* (2006.01)
(Continued)

(52) U.S. Cl.
CPC .............. *A45D 34/04* (2013.01); *A61K 8/046* (2013.01); *A61M 35/00* (2013.01); *A61Q 1/02* (2013.01);
(Continued)

(58) Field of Classification Search
CPC ......... A45D 34/04; A61K 8/04; A61M 35/00; A61Q 1/02; A61Q 1/04; A61Q 1/12; A61Q 17/04; A61Q 19/00
See application file for complete search history.

(56) References Cited

U.S. PATENT DOCUMENTS

| 5,757,498 A | 5/1998 | Klein, II et al. |
| 6,514,504 B1 | 2/2003 | Yen et al. |
| (Continued) | | |

FOREIGN PATENT DOCUMENTS

| CN | 1379656 A | 11/2002 |
| CN | 1638877 A | 7/2005 |
| (Continued) | | |

OTHER PUBLICATIONS

International Search Report, issued in PCT/JP2016/082877. PCT/ISA/210, dated Dec. 27, 2016.
(Continued)

*Primary Examiner* — Tatyana Zalukaeva
*Assistant Examiner* — Ilya Y Treyger
(74) *Attorney, Agent, or Firm* — Birch, Stewart, Kolasch & Birch, LLP.

(57) ABSTRACT

A film forming device 10 including a distance measurement unit 30 for measuring the distance between the skin S and the device 10, a distance decision unit 31 for deciding whether the distance measured by the distance measurement unit 30 is proper for electrostatic spraying, and a distance notification unit 32 for notifying a user of the decision by the distance decision unit 31. The film forming device 10 is of hand-held type small enough and configured to be held by the user's hand. The device 10 preferably includes an angle measurement unit 42 for measuring the angle between the electrostatic spray direction and the skin S.

9 Claims, 11 Drawing Sheets

(51) Int. Cl.

| | | |
|---|---|---|
| *A61M 35/00* | (2006.01) | |
| *A61Q 1/02* | (2006.01) | |
| *A61Q 1/04* | (2006.01) | |
| *A61Q 1/12* | (2006.01) | |
| *A61Q 17/04* | (2006.01) | |
| *A61Q 19/00* | (2006.01) | |
| *B05B 12/00* | (2018.01) | |
| *B05B 12/12* | (2006.01) | |
| *B05B 5/053* | (2006.01) | |
| *B05B 12/08* | (2006.01) | |
| *B05B 5/16* | (2006.01) | |
| *B05B 5/00* | (2006.01) | |
| *B05B 5/025* | (2006.01) | |
| *A45D 44/08* | (2006.01) | |
| *B05B 15/68* | (2018.01) | |

(52) U.S. Cl.
CPC ............... *A61Q 1/04* (2013.01); *A61Q 1/12* (2013.01); *A61Q 17/04* (2013.01); *A61Q 19/00* (2013.01); *B05B 5/006* (2013.01); *B05B 5/025* (2013.01); *B05B 5/053* (2013.01); *B05B 5/0538* (2013.01); *B05B 5/1608* (2013.01); *B05B 5/1691* (2013.01); *B05B 12/004* (2013.01); *B05B 12/084* (2013.01); *B05B 12/12* (2013.01); *B05B 12/124* (2013.01); *A45D 44/08* (2013.01); *A61K 2800/87* (2013.01); *B05B 15/68* (2018.02)

(56) References Cited

U.S. PATENT DOCUMENTS

| | | | |
|---|---|---|---|
| 6,866,212 B2 * | 3/2005 | Sumiyoshi | ............ B05B 5/1691 239/332 |
| 7,105,058 B1 | 9/2006 | Sinyagin | |

| | | | |
|---|---|---|---|
| 2002/0155069 A1 | 10/2002 | Pruche et al. | |
| 2002/0192252 A1 | 12/2002 | Ying Yen et al. | |
| 2004/0021017 A1 | 2/2004 | Sumiyoshi et al. | |
| 2007/0131805 A1 | 6/2007 | Yamaguchi et al. | |
| 2009/0272316 A1 | 11/2009 | Arnaud et al. | |
| 2011/0060195 A1 | 3/2011 | De Noray et al. | |
| 2013/0146684 A1 | 6/2013 | Minakuchi et al. | |

FOREIGN PATENT DOCUMENTS

| | | | |
|---|---|---|---|
| CN | 100475354 C | | 4/2009 |
| CN | 101507966 A | | 6/2009 |
| CN | 103068356 A | | 4/2013 |
| DE | 10003958 A1 | | 8/2001 |
| EP | 1297895 A1 | | 4/2003 |
| JP | 58-17864 A | | 2/1983 |
| JP | 11-218447 A | | 8/1999 |
| JP | 2004-501177 A | | 1/2004 |
| JP | 2006-95332 A | | 4/2006 |
| JP | 2008-188118 A | | 8/2008 |
| JP | 2011-67621 A | | 4/2011 |
| KR | 10-2015-0035238 A | | 4/2016 |
| WO | WO 01/12138 A1 | | 2/2001 |
| WO | WO 01/12335 A1 | | 2/2001 |
| WO | WO2003015728 A1 | * | 5/2002 |
| WO | 2007/079274 A2 | | 7/2007 |
| WO | 2009/091489 A1 | | 7/2009 |

OTHER PUBLICATIONS

Written Opinion of the International Searching Authority, issued in PCT/JP2016/082877, PCT/ISA/237, dated Dec. 27, 2016.
Extended European Search Report, dated May 24, 2019, for European Application No. 16864140.5.

* cited by examiner

COAT-FORMING DEVICE

CROSS REFERENCE TO RELATED APPLICATIONS

This application is the National Phase of PCT/JP2016/082877 filed on Nov. 4, 2016, which claims priority under 35 U.S.C. § 119(a) to Patent Application No. 2015-222336 filed in Japan on Nov. 12, 2015, all of which are hereby expressly incorporated by reference into the present application.

TECHNICAL FIELD

The present invention relates to a film forming device for forming a film on the skin.

BACKGROUND ART

Various methods for forming a film by electrostatic spraying are known. For example, Patent Literature 1 below discloses disposable cartridges for use in electrostatic spraying devices for cosmetic products. The electrostatic spraying device disclosed is of hand-held and self-contained type and used to spray a cosmetic foundation.

Patent Literature 2 below discloses an electrostatic-spray apparatus for applying a cosmetic foundation to the face. The apparatus comprises (a) a reservoir containing the cosmetic foundation to be delivered, (b) a delivery means which is in communication with the reservoir, (c) a high voltage generator generating voltage in the range of 3 kV to 20 kV powered from an electricity source, (d) a control means for applying the high voltage from the high voltage generator to the delivery means, and (e) instructions in association with the apparatus for applying the foundation to the face. The instructions comprise instructions to: (i) keep the end of the nozzle from 9 to 13 cm from the face; (ii) move the nozzle at a steady pace without stopping while the apparatus is operating; (iii) use the faster speed for all-over facial application; and (iv) use the slower speed for spot application, if desired.

CITATION LIST

Patent Literature

Patent Literature 1: WO2001/012335A1
Patent Literature 2: WO2001/012138A1

SUMMARY OF INVENTION

In the formation of a film by electrostatic spraying, it is necessary to form an adequate electric field between the electrostatic spray device and an object on which a film is to be formed. For this, it is effective to keep a constant distance between the spray device and the object. In the case of using a stationary electrostatic spray device, it is relatively easy to keep a constant distance between the device and the object. When in using a hand-held type electrostatic spray device, it is not easy to maintain the distance constant.

The invention provide, in one aspect, a film forming device for forming a film on the skin by electrostatic spraying. The film forming device of the invention includes a distance measurement unit for measuring the distance between the skin on which a film is to be formed and the film forming device, a distance decision unit for deciding whether the distance measured by the distance measurement unit is proper for electrostatic spraying, and a distance notification unit for notifying a user of the decision made by the distance decision unit. The film forming device is of hand-held type that is small enough, and configured, to be held by the hand of a user.

The invention also provides, in another aspect, a film forming device for forming a film on the skin by electrostatic spraying. The film forming device includes a distance measurement unit for measuring the distance between the skin on which a film is to be formed and the film forming device and a voltage control unit for adjusting the output voltage of a high-voltage supply used to carry out electrostatic spraying in accordance with the distance measured by the distance measurement unit. The film forming device is of hand-held type that is small enough, and configured, to be held by the hand of a user.

DESCRIPTION OF EMBODIMENTS

The invention relates to a film forming device using an electrostatic spraying method. More particularly, it relates to a film forming device that allows for easily keeping a constant distance between the device and an object on which a film is to be formed.

Figure 1:
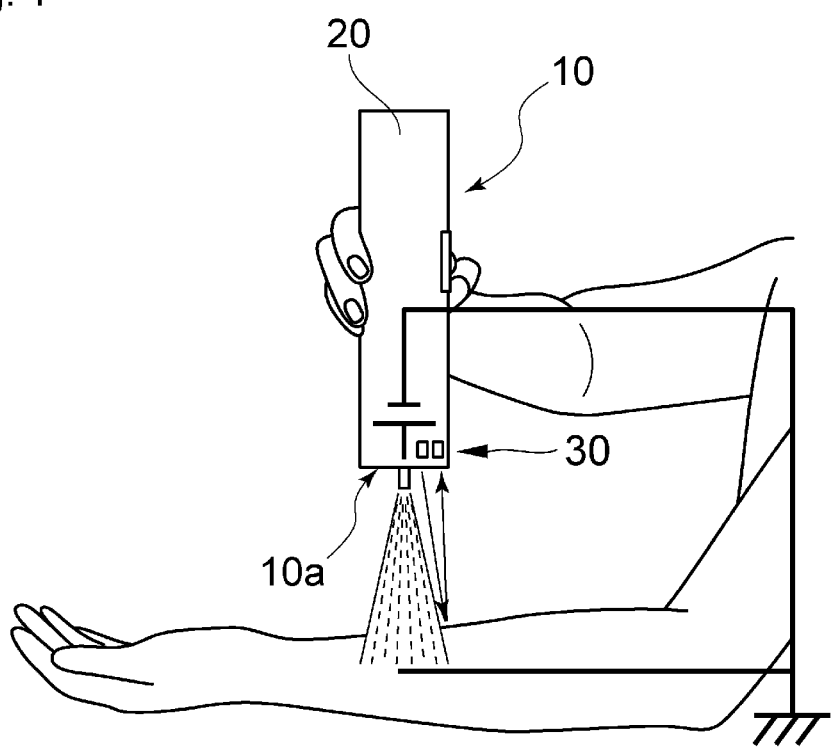
FIG. 1 schematically illustrates an embodiment of the film forming device of the invention.

The invention will be illustrated on the basis of its preferred embodiments with reference to the accompanying drawings. FIG. 1 illustrates an embodiment of the film forming device according to the invention. A film forming device 10 illustrated in FIG. 1 is a device for forming a film on the skin by electrostatic spraying. In the following description the film forming device 10 will also be called an "electrostatic spray device" 10. The electrostatic spray device 10 is of hand-held type with a shape and a size configured to, and small enough to, be held by the user's hand. The electrostatic spray device 10 preferably has a size small enough to be held in one hand. The electrostatic spray device 10 of FIG. 1 has a cylindrical housing 20 in which all the constituent components are contained. The housing 20 has a nozzle (unshown) at one longitudinal end 10a thereof. The nozzle is attached to the housing 20 to project toward the skin with the discharge direction of a spraying composition, which is a film-forming material, coincident with the longitudinal direction of the housing 20. With the tip of the nozzle projecting toward the skin along the longitudinal direction of the housing 20, the spraying composition is less likely to adhere to the housing, enabling stable film formation.

In operating the electrostatic spray device 10, a user who wants to form a film on the user's own skin by electrostatic spraying holds the device 10 by the user's hand to direct the end 10a of the device 10, at which the nozzle (unshown) is disposed, to the target application area. FIG. 1 displays the electrospray device 10 of which the end 10a is directed to the inner side of the user's forearm. In this state, the device 10 is turned on to perform electrostatic spraying. On turning on the device 10, an electric field forms between the nozzle and the skin. In the embodiment shown in FIG. 1, a positive high voltage is applied to the nozzle, and the skin becomes a negative terminal. With the formation of an electric field between the nozzle and the skin, the spraying composition at the tip of the nozzle is polarized by electrostatic induction and forms a corn shape, and charged droplets of the spraying composition are jetted from the tip of the corn into air along the electric field toward the skin. As the solvent evaporates from the charged and jetted spraying composition, the charge density of the surface of the spraying composition increases excessively. Consequently, the spraying composition spreads out in air while repeatedly reducing in droplet size due to Coulomb repulsion and reaches the skin. With the viscosity of the spraying composition adjusted appropriately, the sprayed composition is able to reach the skin in the form of liquid droplets. Alternatively, the solvent which is volatile is evaporated from the composition being jetted into air such that the solute which is a film-forming polymer is drawn into fiber due to difference in potential while being solidified, and the fiber is deposited on the skin. With an increased viscosity, the spraying composition is easy to deposit on the skin in the form of fiber, thereby to form a porous film made up of the deposited fiber on the skin. Such a porous film composed of deposited fiber may also be formed by adjusting the distance between the nozzle and the skin and/or the voltage applied to the nozzle.

Although a large potential difference forms between the nozzle and the skin during electrostatic spraying, the electric current flowing in a human body is extremely minute due to a very high impedance. The inventors have confirmed that the current flowing in the body of a user during electrostatic spraying is a few orders of magnitude smaller than that flowing in a human body due to static electricity generated in daily-life activities.

Figure 2:
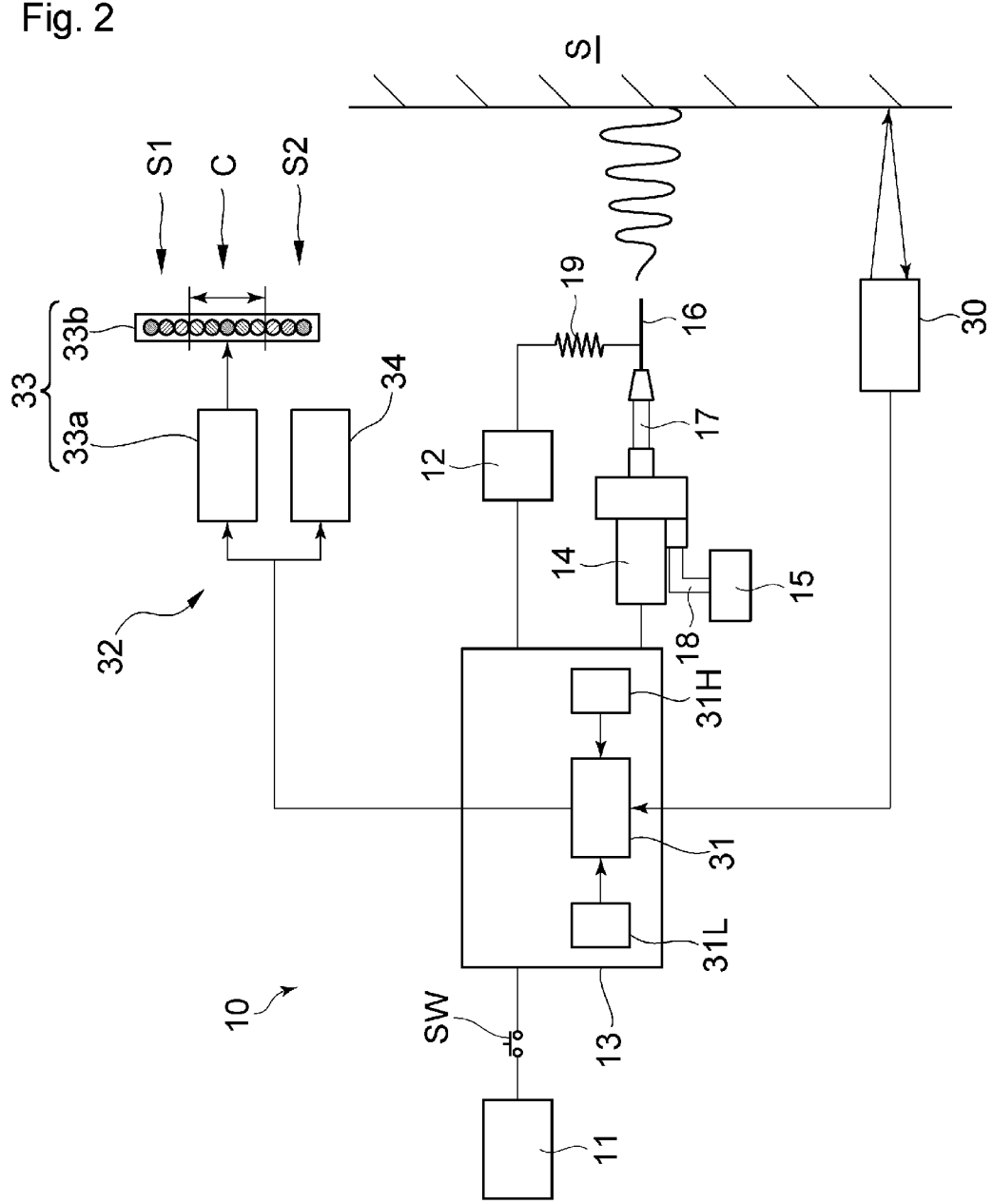
FIG. 2 is a diagram illustrating the configuration of the film forming device shown in FIG. 1.

FIG. 2 is a diagram illustrating the configuration of the electrostatic spray device 10 of FIG. 1. As illustrated, the electrostatic spray device 10 includes a low-voltage supply 11. The low-voltage supply 11 is able to generate a voltage of from several to ten-odd volts. To ensure the portability of the electrostatic spray device 10, the low-voltage supply 11 is preferably one or more battery cells. To use a battery cell(s) as the low-voltage supply 11 offers the advantage of easy replacement when necessary. An AC adaptor or the like may be used as the low-voltage supply 11 in place of batteries.

The electrostatic spray device 10 also includes a high-voltage supply 12. The high-voltage supply 12 is connected to the low-voltage supply 11 and has an electronic circuit (unshown) that boosts the voltage generated by the low-voltage supply 11 to a direct current high voltage of 3 to 20 kV. The booster electronic circuit is usually composed of a transformer, a capacitor, a semiconductor device, and so on.

The electrostatic spray device 10 also includes an auxiliary electric circuit (hereinafter, "auxiliary circuit") 13. The auxiliary circuit 13 includes active electronic devices, such as an integrated circuit, a transistor, an FET, and a diode, and passive electronic devices, such as a resistor and a capacitor, and is composed of a digital circuit and/or an analogue circuit. The auxiliary circuit 13 is intermediate between the low-voltage supply 11 and the high-voltage supply 12 and, on being operated by the low-voltage supply 11, functions to regulate the voltage of the low-voltage supply 11 so that the high-voltage supply 12 operates stably. The auxiliary circuit 13 also functions to control the motor speed of a micro gear pump 14 hereinafter described. To control the motor speed is to control the feed of a spraying composition from a hereinafter described reservoir 15 configured to contain a spraying composition to the micro gear pump 14. A switch SW is provided between the auxiliary circuit 13 and the low-voltage supply 11 so that a user may switch the electrostatic spray device 10 on and off.

The electrostatic spray device 10 further includes a nozzle 16. The nozzle 16 may be made of conductors, such as metals, or non-conductors, such as plastics, rubber, and ceramics, and is configured to jet a spraying composition from its tip. The nozzle 16 has a microspace extending in its longitudinal direction, through which a spraying composition flows. The cross-sectional diameter of the microspace is preferably 100 to 1000 μm. The nozzle 16 connects to the micro gear pump 14 via a tube 17. The tube 17 may be a conductor or a non-conductor. The nozzle 16 has an electric connection to the high-voltage supply 12 so that a high voltage may be applied to the nozzle 16. In order to prevent the nozzle 16 from allowing an excessive current to flow into the body in case of contact with the skin, the nozzle 16 is connected to the high-voltage supply 12 via a current-limiting resistor 19.

The micro gear pump 14 connecting to the nozzle 16 via the tube 17 functions as a feeder for delivering the spraying composition contained in the reservoir 15 to the nozzle 16. The micro gear pump 14 operates on the power supplied from the low-voltage supply 11. The micro gear pump 14 is configured to deliver a predetermined amount of the spraying composition to the nozzle 16 under control by the auxiliary circuit 13.

The reservoir 15 connects to the micro gear pump 14 via a flexible tube 18. The reservoir 15 contains the spraying composition. The reservoir 15 preferably has the form of an easy-to-replace cartridge.

The electrostatic spray device 10 further includes a distance measurement unit 30. The distance measurement unit 30 includes a device capable of measuring the distance between the skin S on which a film is to be formed and the electrostatic spray device 10. To accomplish this purpose, the distance measurement unit 30 is preferably disposed at the longitudinal end 10a of the housing 20 of the electrostatic spray device 10, i.e., the end having the nozzle attached thereto as illustrated in FIG. 1. The distance measurement unit 30 is typically exemplified by, but not limited to, an infrared (IR) distance sensor. An IR distance sensor has a module containing an IR light source, such as an IR LED, and an IR light receiving element and is configured to direct IR light from the IR light source to an object and receive the IR light reflected by the object to determine the distance.

The distance measurement unit 30 is electrically connected to the auxiliary circuit 13. The auxiliary circuit 13 has incorporated therein a distance decision unit 31. The distance decision unit 31 is composed of hardware using an integrated circuit and the like or software run on the hardware. The distance decision unit 31 functions to decide whether the distance measured by the distance measurement unit 30 is proper for electrostatic spraying. The distance decision unit 31 is equipped with an upper limit input/memory unit 31H and a lower limit input/memory unit 31L. The upper limit is a predetermined upper limit of the distance between the skin S and the electrostatic spray device 10. If the distance exceeds the upper limit, electrostatic spraying cannot be carried out successfully. The lower limit is a predetermined lower limit of the distance between the skin S and the electrostatic spray device 10. If the distance is shorter than the lower limit, electrostatic spraying cannot be performed successfully.

The distance between the skin S and the electrostatic spray device 10 as measured by the distance measurement unit 30 is converted to an electrical signal, which is transmitted to the distance decision unit 31 of the auxiliary circuit 13. On receipt of the distance data, the distance decision unit 31 decides whether the distance as measured is proper for effecting electrostatic spraying. Specifically, it decides whether the distance as measured is in the set range between the upper and the lower limit. The electrostatic spray device 10 is configured to inform a user of the result of the decision made by the distance decision unit 31. Specifically, the device 10 further includes a distance notification unit 32 that notifies a user of the decision made by the distance decision unit 31. The distance notification unit 32 has a distance indicator 33 that notifies a user of the distance by lighting lamps and an alarm 34 that notifies a user of the distance by sound or vibration.

The distance indicator 33 is composed of a drive circuit 33a and an LED array 33b driven by the drive circuit 33a. The drive circuit 33a is an electronic circuit having an active device, such as a transistor and an FET. The LED array 33b is composed of a plurality of LEDs (light-emitting diodes) arrayed in a single line. The plurality of LEDs composing the LED array 33b emit light of difference colors according to the location. For example, two or more LEDs located in the middle region C of the array 33b can be those emitting green light, while two or more LEDs located on either side of the middle region C, i.e., side regions S1 and S2 can be those emitting red to orange light. The array 33b can be configured such that one or more LEDs located in the middle region C light up when the distance between the skin S and the electrostatic spray device 10 measured by the distance measurement unit 30 is between the upper and the lower limit. In this case, any one of the LEDs located in the middle region C may light up to enable a user to visually recognize the degree of deviation from the proper distance, depending on the distance between the skin S and the electrostatic spray device 10.

In the case when the distance between the skin S and the electrostatic indicator device 10 as measured by the distance measurement unit 30 is above the upper limit or below the lower limit, the LED array 33b may be configured such that one or more LEDs located in the side region S1 or S2 light up. In this case, any one of the LEDs located in the side region S1 or S2 may light up to enable a user to visually recognize the degree of deviation from the proper distance, depending on the distance between the skin S and the electrostatic spray device 10.

The alarm 34 composing the distance notification unit 32 together with the distance indicator 33 functions to notify a user of the distance by sound or vibration. To achieve the function, the alarm 34 may be equipped with a buzzer or a speaker or a vibration motor. The tone of sound or the frequency, amplitude, or rhythm of the vibration can be varied according to the distance between the skin S and the electrostatic spray device 10.

The configuration of the electrostatic spray device 10 of the present embodiment enables a user to perceive the distance between the skin S and the device 10 through acoustic or haptic sense and, based on the perception, keep a proper distance between the skin S and the device 10 during electrostatic spraying. Thus, an adequate electric field is formed between the skin S and the device 10, allowing a user to perform electrostatic spraying successfully.

Figure 3:
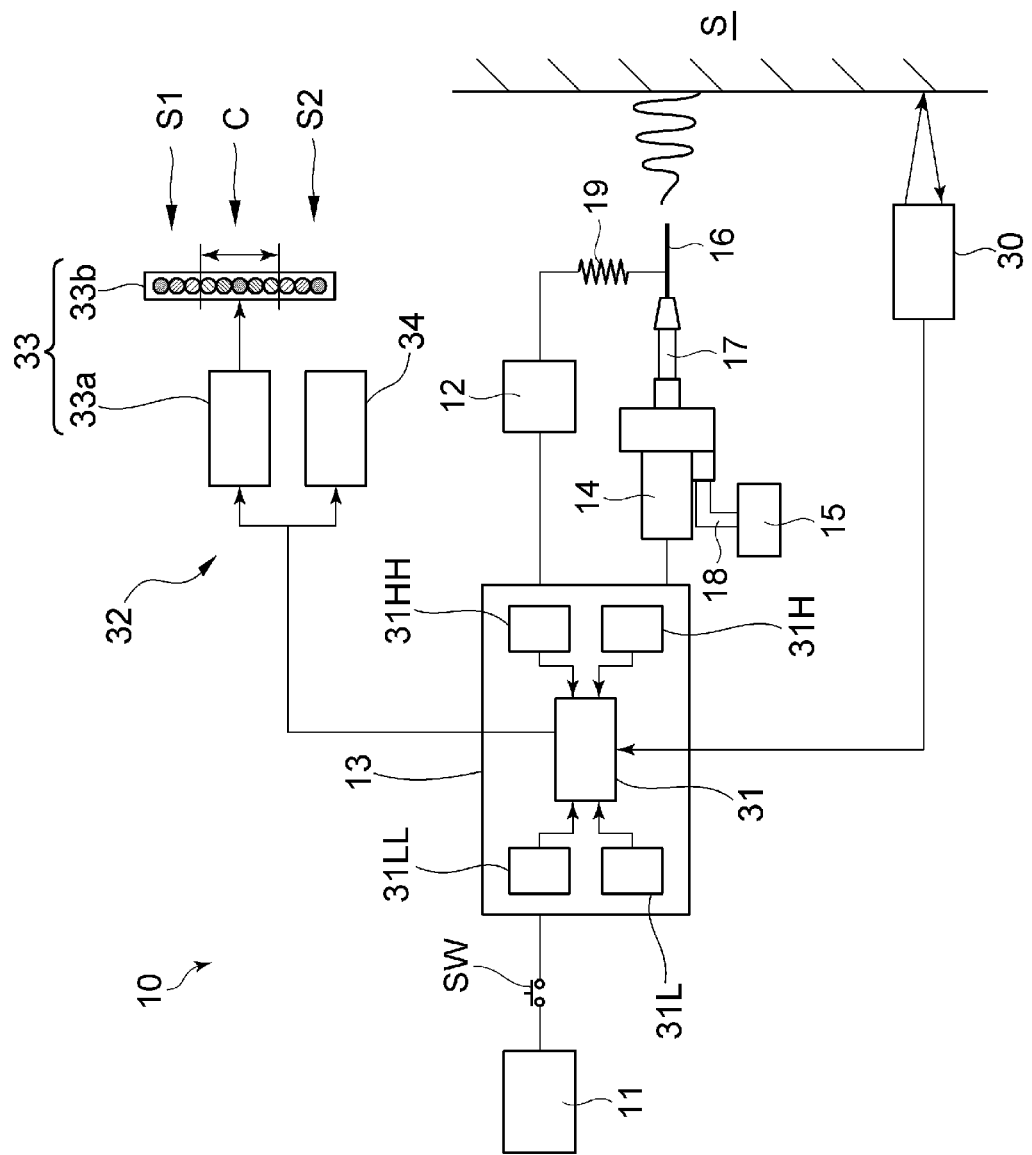
FIG. 3 is a diagram illustrating the configuration of another embodiment of the film forming device of the invention (equivalent to FIG. 2).

The electrostatic spray device 10 of the embodiment may further has a stop function for stopping the electrostatic spraying in the event of a deviation of the distance between the skin S on which a film is to be formed and the device 10 from the set range during electrostatic spraying. Such a function may be incorporated into, for example, the auxiliary circuit 13 of the device 10. For example, as illustrated in FIG. 3, the distance decision unit 31 may further be equipped with an upper stop limit input/memory unit 31HH and a lower stop limit input/memory unit 31LL in addition to the upper limit input/memory unit 31H and lower limit input/memory unit 31L. The distance decision unit 31 is configured to emit a signal to stop electrostatic spraying when the distance between the skin S and the device 10 is above the upper stop limit or below the lower stop limit. On receipt of the stop signal, the auxiliary circuit 13 forcedly stops the high-voltage supply 12 from boosting the voltage and, at the same time, forcedly stops the micro gear pump 14 from delivering the spraying composition. This configuration effectively prevents inconveniences, such as the spraying composition's spreading out of the target application area and the spraying composition's bouncing back from the skin S to adhere the device 10.

Figure 4:
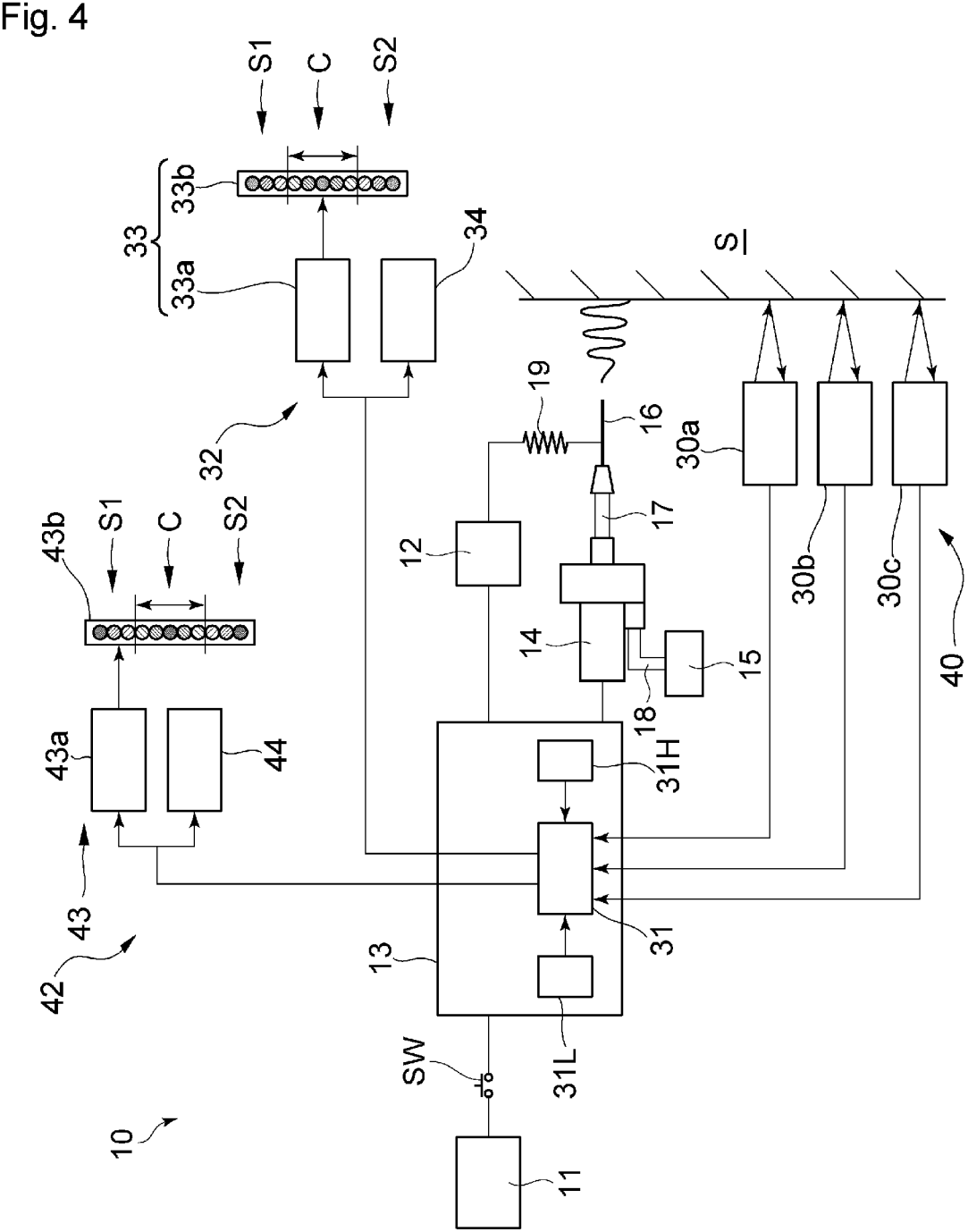
FIG. 4 is a diagram illustrating the configuration of still another embodiment of the film forming device of the invention (equivalent to FIG. 2).

FIG. 4 illustrated another embodiment of the electrostatic spray device of the invention. The description of the embodiments hereinafter described, including the embodiment illustrated in FIG. 4, will generally be confined to the differences from the embodiment illustrated in FIGS. 1 through 3. Otherwise, the description of the embodiment of FIGS. 1 through 3 applies appropriately to the other embodiments. The members in FIG. 4 and subsequent figures that are the same as those in FIGS. 1 to 3 are given the same numerals or references as in FIGS. 1 to 3.

The electrostatic spray device 10 illustrated in FIG. 4 has the same configuration as that shown in FIG. 2 and further includes an angle measurement unit 40 that measures the angle formed between the electrostatic spraying direction and the skin S. The angle measurement unit 40 is composed of a plurality of distance measurement units 30a, 30b, . . . . In the embodiment shown in FIG. 4, the angle measurement unit 40 is composed of three distance measurement units 30a, 30b, and 30c. The three distance measurement units 30a, 30b, and 30c are preferably arranged at the vertices of a regular triangle when viewed from the longitudinal end 10a of the electrostatic spray device 10 shown in FIG. 1.

Being so arranged, the distance measurement units 30a, 30b, and 30c each determine the distance between the skin S and the device 10.

The data of the distance between the skin S and the electrostatic spray device 10 measured with the distance measurement units 30a, 30b, and 30b are transmitted in the form of electrical signals to the distance decision unit 31 of the auxiliary circuit 13. On receiving the distance data, the distance decision unit 31 functions to decide whether there is any difference between the received distance data. When the difference in the distance data is within a predetermined range, the distance decision unit 31 decides that the angle between the direction of the electrostatic spray and the skin S is a right angle and that the distance as measured is the distance between the skin S and the device 10. In this case, the distance decision unit 31 further decides whether the distance is proper to effect electrostatic spraying. When the difference between the distance data from the three measurements units 30a, 30b, and 30c exceeds the predetermined range, the angle between the direction of the electrostatic spray and the skin S is decided not to be a right angle. In this case, the distance between the skin S and the device 10 is not decided.

The electrostatic spray device 10 is configured to inform a user of the result of decision by the distance decision unit 31. Specifically, the electrostatic spray device 10 includes an angle notification unit 42 in addition to the distance notification unit 32. As described earlier, the distance notification unit 32 has the distance indicator 33 and the alarm 34. The angle notification unit 42 has an angle indicator 43 and an alarm 44. The angle indicator 43 functions to inform a user of the angle by lighting lamps. The alarm 44 functions to inform a user of the angle by sound or vibration. The angle indicator 43 is composed of a drive circuit 43a and an LED array 43b driven by the drive circuit 43a. The drive circuit 43a and LED array 43b may have the same configuration as the drive circuit 33a and the LED array 33b of the distance indicator 33 of the distance notification unit 32. The alarm 44 may have the same configuration as the alarm 34 of the distance notification unit 32.

Film formation on the skin S by the use of the electrostatic spray device 10 of the embodiment can be carried out as follows. The device 10 is held with the longitudinal end 10a of the housing 20 directed to the skin S on which a film is to be formed. In this state, the distance measurement units 30a, 30b, and 30c operate to determine the angle θ between the longitudinal direction of the housing 20, i.e., the direction of the electrostatic spray and the skin S. The LED array 43b is configured such that one or more LEDs located in the middle region C of the array 43b light up when the angle θ is decided to be a right angle. In this case, any one of the LEDs located in the middle region C may light to enable a user to visually recognize the degree of deviation from 90 degrees, depending on the angle θ between the skin S and the electrostatic spray direction. On the other hand, the LED array 43b is configured such that one or more LEDs located in either of the side regions S1 and S2 light up when the angle θ between the electrostatic spray direction and the skin S deviates from 90 degrees. In this case, any one of the LEDs located in the side region S1 or S2 may light up to enable a user to visually recognize the degree of deviation from 90 degrees, depending on the degree of deviation of the angle θ from 90 degrees.

The alarm 44 composing the angle notification unit 42 together with the angle indicator 43 is configured to generate sound or vibration and functions to notify a user of the degree of deviation of the angle θ between the electrostatic spray direction and the skin S from 90 degrees by sound or vibration similarly to the alarm 34 of the distance notification unit 32 described above. The tone of sound or the frequency, amplitude, or rhythm of the vibration can be varied according to the degree of deviation of the angle between the electrostatic spray direction and the skin S from 90 degrees.

The electrostatic spray device 10 also notifies a user of the distance between the skin S and the device 10 as well as the angle θ. The mechanism of notification may be the same as in the embodiment illustrated in FIG. 2.

The configuration of the electrostatic spray device 10 of the present embodiment enables a user to perceive the distance between the skin S and the device 10 through acoustic or haptic sense and, based on the perception, keep a proper distance between the skin S and the device 10 during electrostatic spraying. In addition to this, the device 10 enables a user to perceive the angle θ between the electrostatic spray direction and the skin S through acoustic or haptic sense and, based on the perception, keep a right angle between the electrostatic spray direction and the skin S during operation. Thus, a more proper electric field is formed between the skin S and the device 10, allowing a user to perform electrostatic spraying more successfully. If the angle θ between the electrostatic spray direction and the skin S deviates from a right angle, the electric field intensity on the part of the skin closest to the nozzle becomes relatively high so that the liquid droplets or fibers produced by electrostatically spraying the spraying composition tend to be concentrated onto that part, whilst the electric field intensity on the part of the skin farther from the nozzle becomes relatively weak so that the droplets or fibers are less deposited on that part. As a result, the coating film formed on the skin tends to have non-uniform thickness. It is therefore important to maintain the angle θ at a right angle in order to form the film with a uniform thickness.

While in the above described embodiment three distance measurement units 30a, 30b, and 30c are used to determine the distance and angle, this measurement system may be replaced with a system including one distance measurement unit and a separate angle measurement unit to measure the distance and the angle separately.

Figure 5:
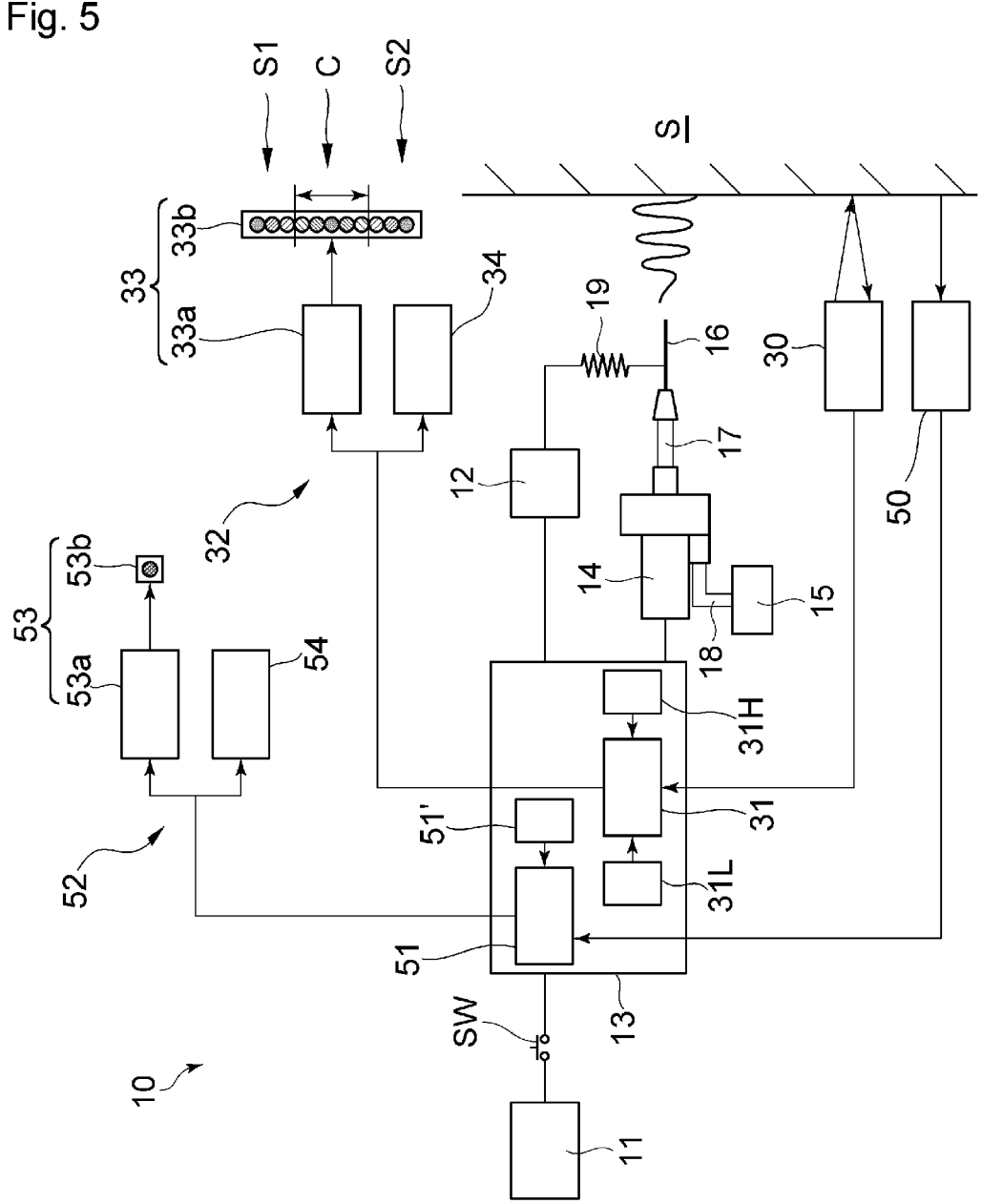
FIG. 5 is a diagram illustrating the configuration of still another embodiment of the film forming device of the invention (equivalent to FIG. 2).

The electrostatic spray device 10 illustrated in FIG. 5 has the same configuration as that shown in FIG. 2 and further includes a color detection unit 50 that detects the color of the film formed by electrostatic spraying. The color detection unit 50 is composed of a device capable of measuring the color of the film being formed. The color detection unit 50 can be a system including a light emitter that irradiates an object with light of three primary colors (e.g., a red LED, a green LED, and a blue LED), a light sensor that receives light reflected on the object (e.g., a photodiode) to output the light intensity, and a calculator that calculates a colorimetric value on the basis of the reflected light intensity for each of the three primary colors. The color detection unit 50 is exemplified by those described in JP 11-218447A.

The color detection unit 50 is electrically connected to the auxiliary circuit 13 mentioned above. The auxiliary circuit 13 has incorporated therein a color decision unit 51. The color decision unit 51 is composed of hardware using an integrated circuit and the like or software run on the hardware. The color decision unit 51 functions to decide whether the color measured by the color detection unit 50 is within a predetermined set range. The color decision unit 51 is equipped with a setting input/memory unit 51'. The setting is a value obtained by quantifying a desired color of film to be formed. If the color of the film formed deviates from the setting, the film formed tends to have poor color integration with skin S.

The color of the film measured by the color detection unit 50 is sent in the form of electrical signal to the color decision unit 51 of the auxiliary circuit 13. On receiving the color data, the color decision unit 51 decides whether the measured color agrees with a preset color, more specifically, whether the deviation of the measured color from the preset color is within a predetermined range. The electrostatic spray device 10 is configured to notify a user of the result of the decision made by the color decision unit 51. Specifically, the device 10 further includes a color notification unit 52 that notifies a user of the decision made by the color decision unit 51. The color notification unit 52 has a color indicator 53 that notifies a user of the color of the film by lighting a lamp and an alarm 54 that notifies a user of the color of the film by sound or vibration.

The color indicator 53 is composed of a drive circuit 53*a* and an LED 53*b* driven by the drive circuit 53*a*. The drive circuit 53*a* is composed of an electronic circuit having an active device, such as a transistor and an FET. The LED 53*b* includes one or more LEDs. The color indicator 53 is configured to light the LED 53*b* when the deviation of the color of the film measured by the color detection unit 50 from the setting is within a predetermined range. If, on the other hand, the deviation exceeds the predetermined range, the LED 53*b* is not lit up.

The alarm 54 that composes the color notification unit 52 together with the color indicator 53 functions to notify a user of the color of the film being formed by sound or vibration. The alarm 54 can be configured to generate sound or vibration when the deviation of the color of the film from the setting is in the predetermined range. On the other hand, the alarm 54 can be configured to stop the sound or vibration when the deviation exceeds the setting. The tone of sound or the frequency, amplitude, or rhythm of vibration can be varied according to the degree of deviation of the color of the film from the setting.

The configuration of the electrospray device 10 of the present embodiment enables a user to perceive the distance between the skin S and the device 10 through acoustic or haptic sense and, based on the perception, keep a proper distance between the skin S and the device 10 during electrostatic spraying. Thus, a proper electric field is formed between the skin S and the device 10, allowing a user to perform electrostatic spraying successfully. In addition to this, the device 10 enables a user to perceive the color of the film being formed through acoustic or haptic sense and, as a result, formation of a film with poor color integration with skin S can be less likely to occur.

Figure 6:
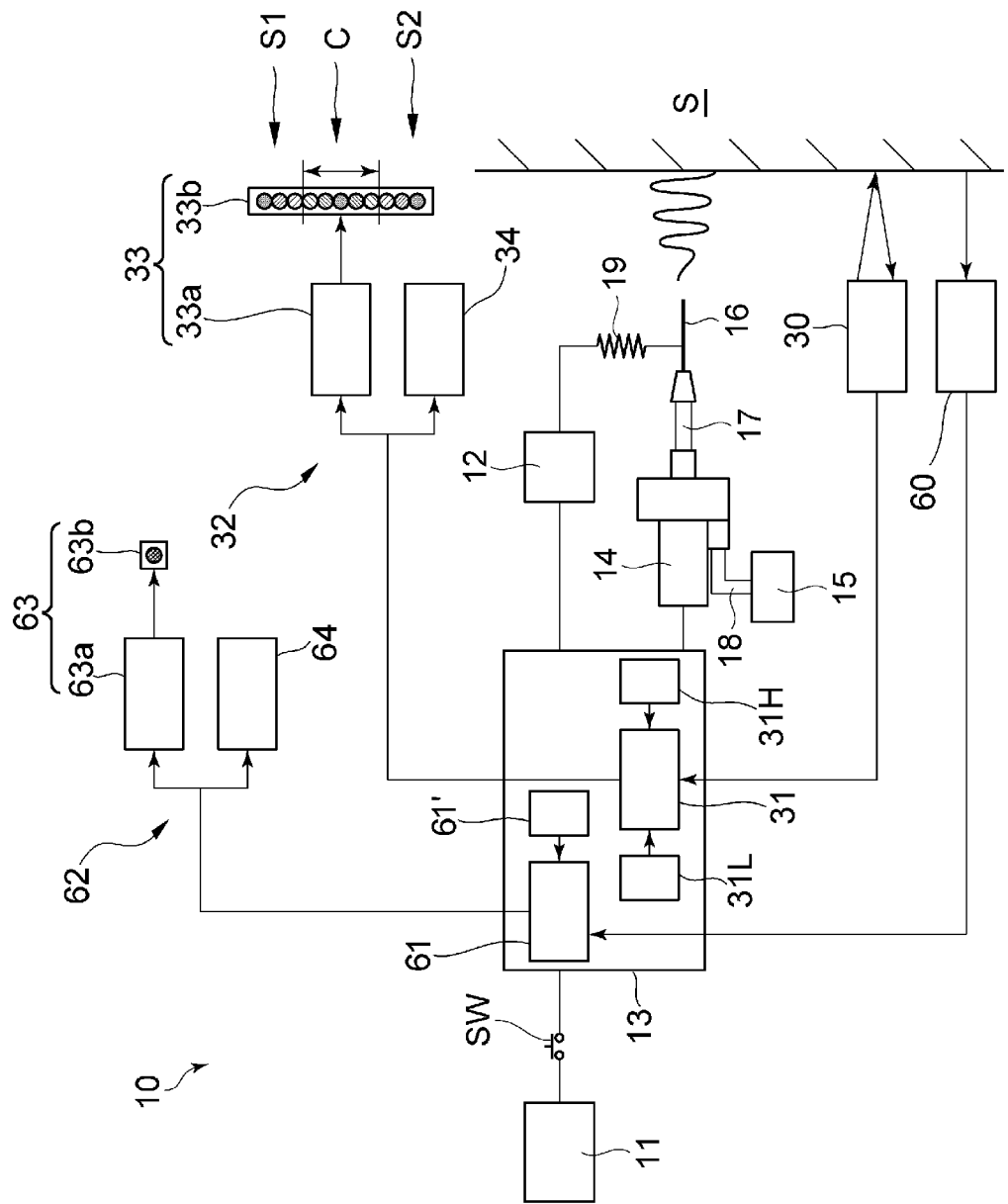
FIG. 6 is a diagram illustrating the configuration of still another embodiment of the film forming device of the invention (equivalent to FIG. 2).

The electrostatic spray device 10 illustrated in FIG. 6 has the same configuration as that shown in FIG. 2 and further includes a smoothness detection unit 60 that detects the smoothness of the film being formed by electrostatic spraying. The smoothness detection unit 60 is composed of a device capable of measuring the smoothness of the film formed. Known devices may be utilized as the smoothness detection unit 60, such as the smoothness evaluation device described in JP 2009-297295A, the texture evaluation device described in JP 2015-46698A, and defect inspection systems for industrial use. According to the disclosure of JP 2009-297295A, for example, smoothness is evaluated by the method comprising the steps of:

(1a) forming a surface-reflected light image and/or internal scattered light image using polarized light, decomposing the surface-reflected light image and/or internal scattered light image into images of a plurality of levels of different frequency bands, and obtaining the basic statistics of the decomposed images, (1b) obtaining a mean luminance of a normal image, (1c) obtaining a subjective evaluation value of smoothness of the skin, (2) conducting multi-regression analysis on the subjective evaluation value of skin smoothness in (1c) with respect to the basic statistics in (1a) and the mean luminance of the normal image in (1b), and (3) acquiring a subjective evaluation value of the smoothness of the skin of a subject from the basic statistics of the surface-reflected light image and/or the internal scattered light image of the subject's skin and the mean luminance of the normal image on the basis of the regression formula obtained in (2).

The smoothness detection unit 60 is electrically connected to the auxiliary circuit 13. The auxiliary circuit 13 has incorporated therein a smoothness decision unit 61. The smoothness decision unit 61 functions to decide whether the smoothness of the film measured by the smoothness detection unit 60 is in a set range. The smoothness decision unit 61 is equipped with a setting input/memory unit 61'. The setting is a value obtained by quantifying desired smoothness of the film to be formed. If the smoothness of the film formed deviates from the setting, the film formed tends to have poor visual integration with the skin S.

The smoothness data of the film acquired by the smoothness detection unit 60 is sent to the smoothness decision unit 61 of the auxiliary circuit 13. On receiving the smoothness data, the smoothness decision unit 61 decides whether the measured smoothness agrees with a preset smoothness, more specifically, whether the deviation of the measured smoothness from the setting is within a predetermined range. The electrostatic spray device 10 is configured to notify a user of the decision made by the smoothness decision unit 61. Specifically, the device 10 further includes a smoothness notification unit 62 that notifies a user of the decision made by the smoothness decision unit 61. The smoothness notification unit 62 has a smoothness indicator 63 that notifies a user of the smoothness of the film by lighting a lamp and an alarm 64 that notifies a user of the smoothness of the film by sound or vibration.

The smoothness indicator 63 is composed of a drive circuit 63*a* and an LED 63*b* driven by the drive circuit 63*a*. The smoothness indicator 63 is configured to light the LED 63B when the deviation of the smoothness of the film measured by the smoothness detection unit 60 from the setting is within the predetermined range. If, on the other hand, the deviation exceeds the predetermined range, the LED 63B does not light.

The alarm 64 that composes the smoothness notification unit 62 together with the smoothness indicator 63 functions to notify a user of the smoothness of the film being formed by sound or vibration. The alarm 64 is configured to generate sound or vibration when the deviation of the smoothness of the film from the setting is in the predetermined range. On the other hand, the alarm 64 is configured to stop the sound or vibration when the deviation from the setting is out of the predetermined range. The tone of sound or the frequency, amplitude, or rhythm of vibration can be varied according to the degree of deviation of the smoothness of the film from the setting.

The configuration of the electrospray device 10 of the present embodiment enables a user to perceive the distance between the skin S and the device 10 through acoustic or haptic sense and, based on the perception, keep a proper distance between the skin S and the device 10 during electrostatic spraying. Thus, an appropriate electric field is formed between the skin S and the device 10, allowing a user to perform electrostatic spraying successfully. In addition to this, the device 10 enables a user to perceive the smoothness of the film being formed through acoustic or haptic sense and, as a result, formation of a film with poor visual integration with the skin S is less likely to occur.

Figure 7:
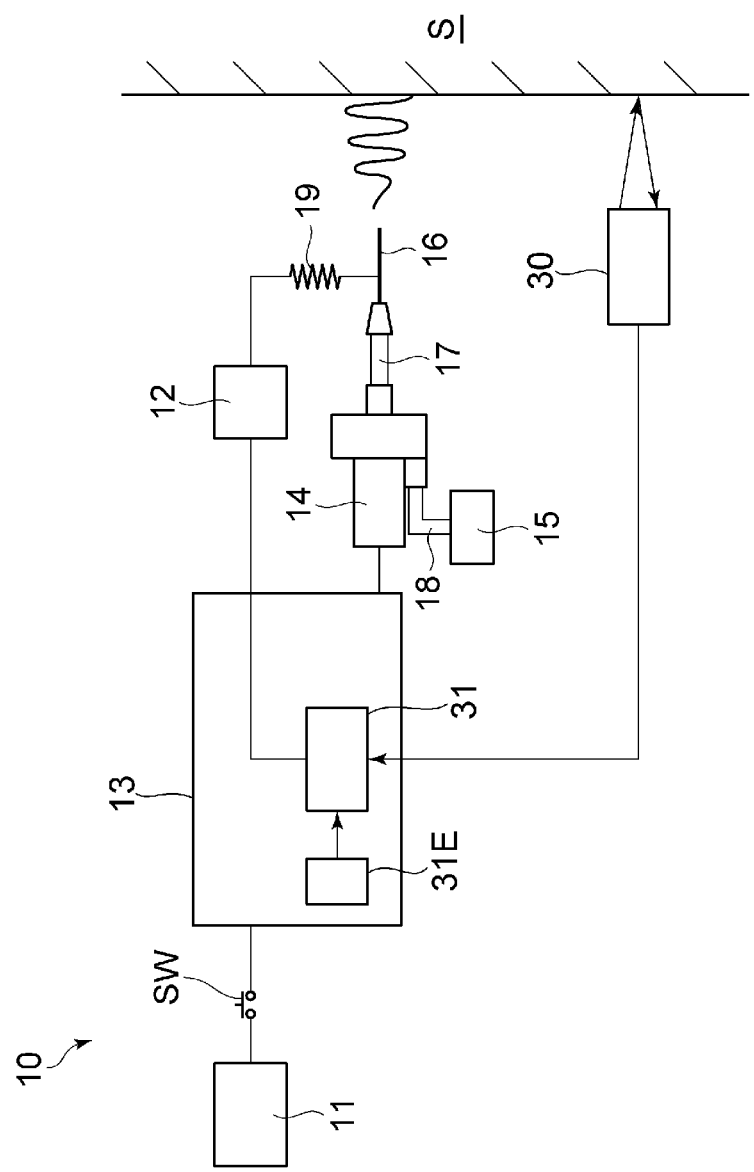
FIG. 7 is a diagram illustrating the configuration of still another embodiment of the film forming device of the invention (equivalent to FIG. 2).

The electrostatic spray devices according to the foregoing embodiments are designed to keep a constant intensity of the electric field formed between the skin S and the device 10 by keeping a constant distance between the skin S and the device 10. Unlike these embodiments, the electrostatic spray device 10 illustrated in FIG. 7 is configured to keep the electric field intensity constant on the presumption that the distance between the skin S and the device 10 can vary. That is, the device 10 is configured to control the applied voltage in accordance with the change of the distance.

The electrostatic display device 10 illustrated in FIG. 7 has a distance measurement unit 30 and a distance decision unit 31. The distance decision unit 31 is equipped with an optimum electric field intensity input/memory unit 31E. The distance decision unit 31 is connected to a high-voltage supply 12 having a voltage control unit. The voltage control unit functions to vary the output voltage depending on the input signal. The high-voltage supply 12 is configured to change the voltage depending on the signal transmitted from the distance decision unit 31.

The optimum electric field intensity is decided as follows. (1) Electrostatic spraying is performed at a varied voltage with a fixed distance D between the skin S and the device 10. (2) A voltage at which the best film is formed, i.e., the optimum voltage V, is decided. (3) An optimum electric field intensity E is calculated from V/D (the optimum voltage V/distance D), and the value calculated is inputted.

Film formation using the electrostatic spray device 10 of the embodiment is carried out as follows. The device 10 is operated to start measurement of the distance between the skin S and the device 10. The distance decision unit 31 calculates the voltage V to be applied from the measured distance on the basis of the relation: E=V/D. The distance decision unit 31 delivers a voltage change signal to the high-voltage supply 12 so that the voltage outputted from the high-voltage supply 12 may agree with the calculated voltage V to be applied. On receipt of the signal, the high-voltage supply 12 changes the output voltage to the voltage V. In this way, the electric field intensity is maintained constant even with variations in the distance between the skin S and the device 10, whereby electrostatic spraying can be conducted successfully.

The electrostatic spray device 10 illustrated in FIG. 7 may further include any one of, or any combination of two or more of, the units and functions possessed by the aforementioned embodiments, such as the stop function used in the embodiment shown in FIG. 3, the angle measurement unit of the embodiment shown in FIG. 4, the color detection unit of the embodiment shown in FIG. 5, and the smoothness detection unit of the embodiment shown in FIG. 6.

Figure 8:
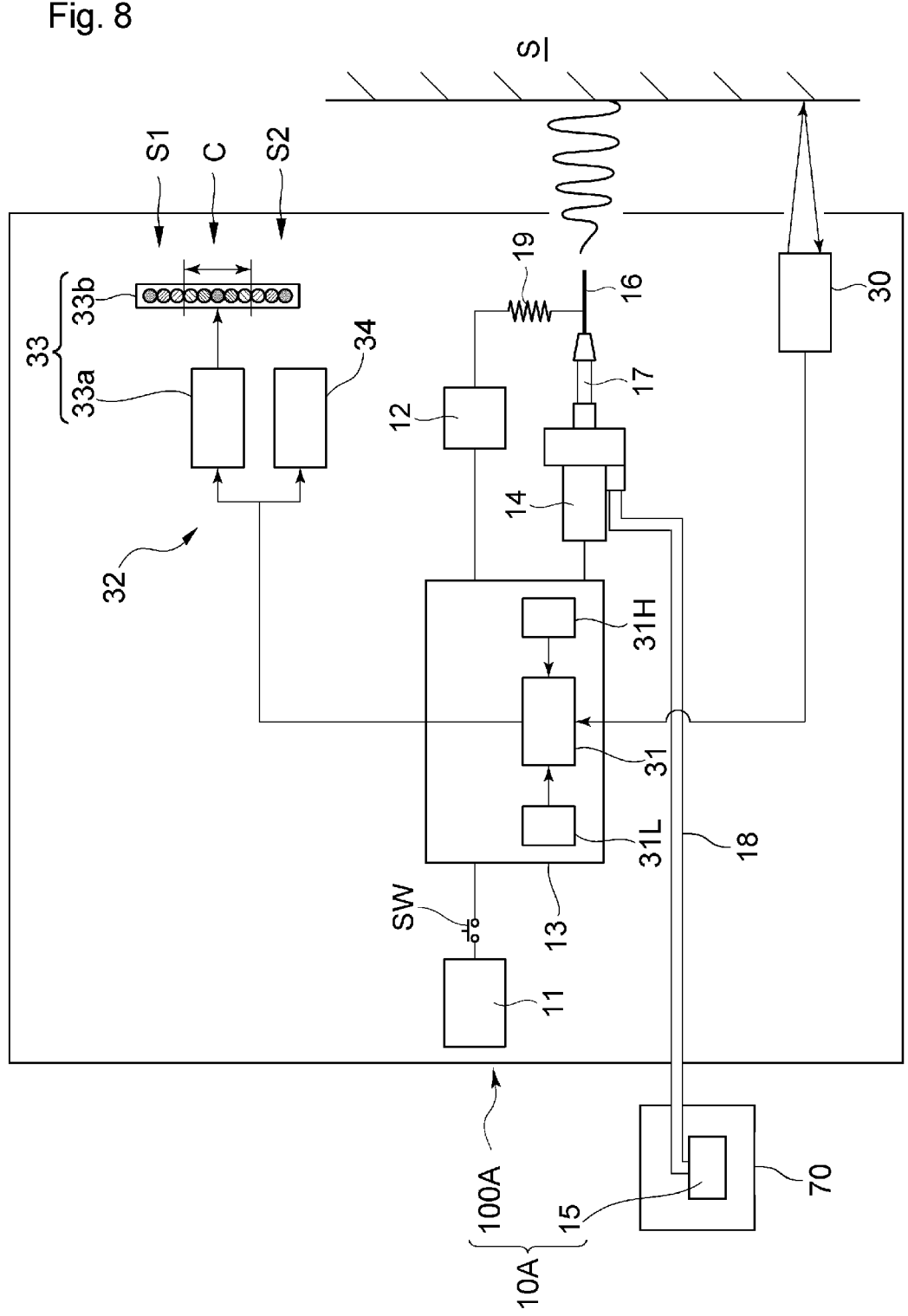
FIG. 8 is a diagram illustrating the configuration of still another embodiment of the film forming device of the invention (equivalent to FIG. 2).

The electrostatic spray device 10A of the embodiment illustrated in FIG. 8 is of separate type unlike the devices of the foregoing embodiments. Specifically, the electrostatic spray device 10A includes a hand-held electrostatic spray device main body (hereinafter simply "main body") 100A and a reservoir 15 separate from the main body 100A and configured to contain a spraying composition for electrostatic spraying. While in the foregoing embodiments the reservoir 15 is embedded in the main body of the electrostatic spray device 100, the reservoir 15 of the present embodiment is externally attached to the main body 100A. The reservoir 15 is contained within a housing 70 separate from the main body 100A. The main body 100A and the reservoir 15 are connected to each other via a flexible tube 18. According to this embodiment, the reservoir 15, being external to the main body 100A, has no capacity limitation. Therefore, the electrostatic spray device 10A of the embodiment is advantageous when a user wants to form a film over a large application area or to spray for a long period of time. The housing 70 containing the external reservoir 15 is preferably lightweight and portable rather than stationary so that a user is allowed to place the housing 70 at the user's feet, on a table, or anywhere a user likes, thus providing highly improved convenience of use. In addition, to use the external reservoir 15 enables further reduction in size of the main body 100A, which provides improved convenience of use and reduced user's burden.

Figure 9:
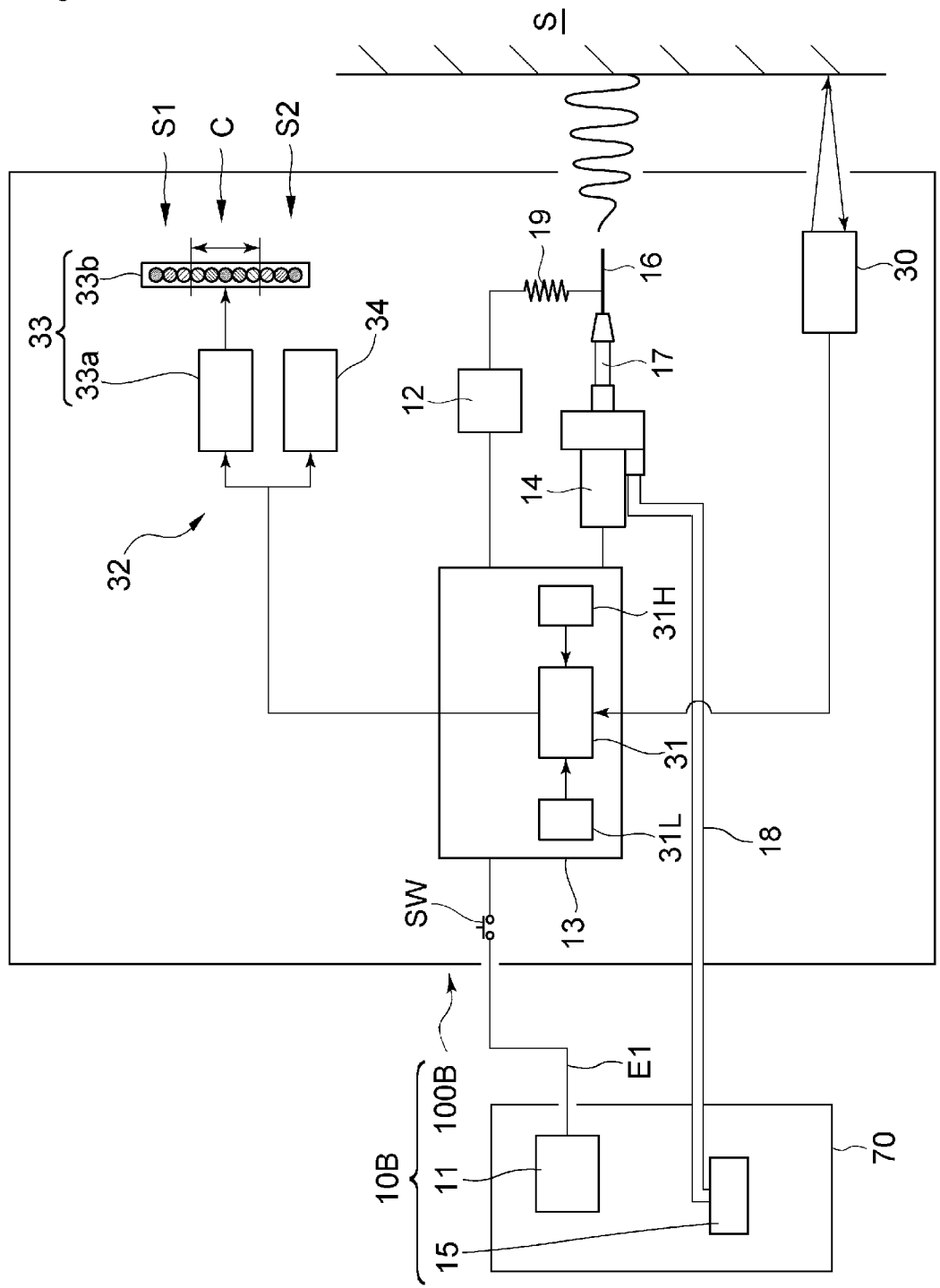
FIG. 9 is a diagram illustrating the configuration of still another embodiment of the film forming device of the invention (equivalent to FIG. 2).

The electrostatic spray device 10B illustrated in FIG. 9 is a modification of the embodiment illustrated in FIG. 8. As illustrated in FIG. 9, the low-voltage supply 11 for driving the main body 100B may be contained within the external housing 70. In this case, the low-voltage supply 11 and the main body 100B may be connected via an electric wire E1. This configuration enables further reduction in size and weight of the main body 100B. In the embodiment of FIG. 9, the flexible tube 18 connecting the reservoir 15 to the main body 100B and the electric wire E1 connecting the low-voltage supply 11 to the main body 100B may be contained together in a single flexible tube.

Figure 10:
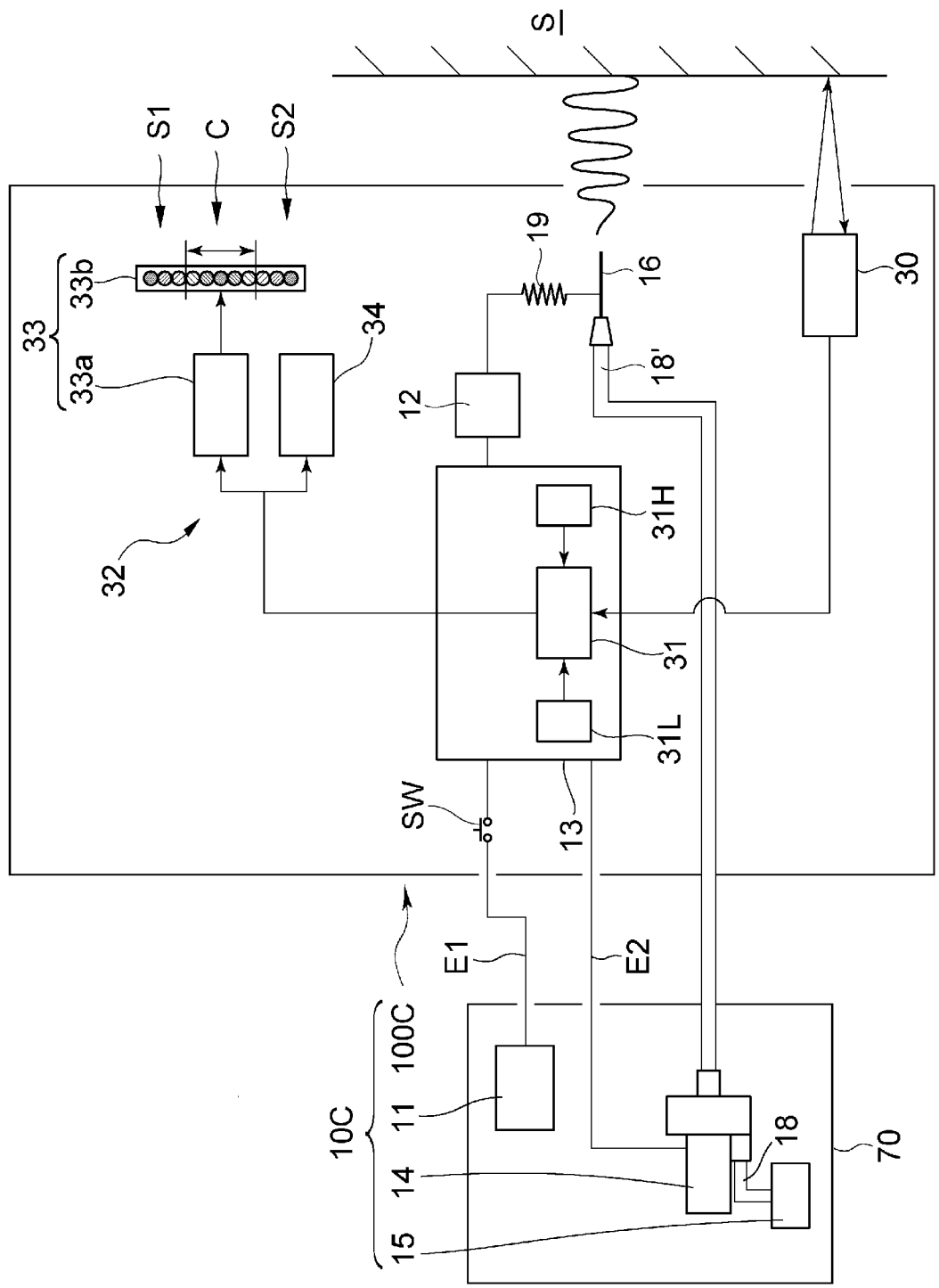
FIG. 10 is a diagram illustrating the configuration of still another embodiment of the film forming device of the invention (equivalent to FIG. 2).

The electrostatic spray device 10C of the embodiment illustrated in FIG. 10 has the same configuration as that shown in FIG. 9, except that the micro gear pump 14 that delivers the spraying composition contained in the reservoir 15 to the main body 100C as a feeder is placed within the external housing 70. The micro gear pump 14 is connected to the main body 100C via an electric wire E2. The outlet side of the micro gear pump 14 is connected to the main body 100C via a flexible tube 18'. According to this embodiment, the main body 100C can have a smaller size and a lighter weight than the main body 100B of the embodiment shown in FIG. 9, providing further improved convenience of use.

In the present embodiment, the low-voltage supply 11 for driving the main body 100C is located in the external housing 70 similarly to the embodiment of FIG. 9. The low-voltage supply 11 and the main body 100C are connected to each other via the electric wire E1. This configuration secures further reduction in size and weight of the main body 100C.

Both the electric wire E2 connecting the main body 100C and the micro gear pump 14 and the flexible tube 18' may be placed together in a single flexible tube. All of the electric wire E2, the flexible tube 18', and the electric wire E1 connecting the low-voltage supply 11 and the main body 100C to each other may be placed together in a single flexible tube. Such a tubing configuration improves handling of the main body 100C.

Figure 11:
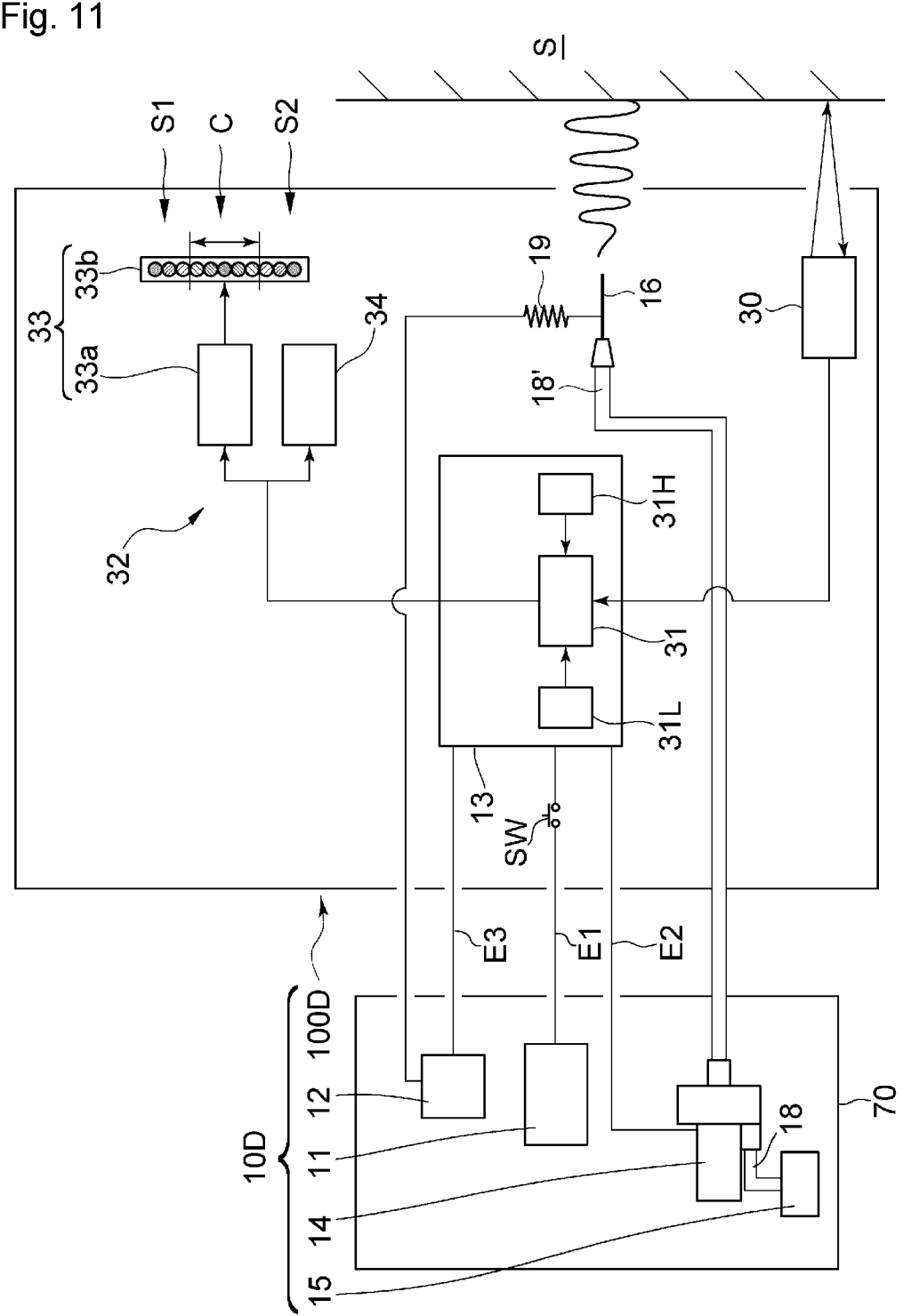
FIG. 11 is a diagram illustrating the configuration of still another embodiment of the film forming device of the invention (equivalent to FIG. 2).

The electrostatic spray device 10D of the embodiment illustrated in FIG. 11 has the same configuration as the embodiment of FIG. 10, except that the high-voltage supply 12 generating a high voltage to perform electrostatic spraying is contained in the external housing 70. The high-voltage supply 12 is connected to the main body 100D via an electric wire E3. Because the high-voltage supply 12 usually contains inside a heavy part such as a transformer and thus is heavy, to place it in the external housing 70 brings about ultimate reduction in size and weight of the main body 100D. In the embodiment, all of the electric wire E1 connecting the low-voltage supply 11 and the main body 100D, the electric wire E2 connecting the main body 100D and the micro gear pump 14, the flexible tube 18', and the wire E3 connecting the high-voltage supply 12 and the main body 100D may be put together in a single flexible tube, whereby the handling of the main body 100D will be further improved.

While the embodiment shown in FIG. 11 represents an example in which the high-voltage supply 12 of the embodiment shown in FIG. 10 is placed in the external housing 70, the placement of the high-voltage supply 12 in the external housing 70 may be applied to the embodiments illustrated in FIGS. 8 and 9. Furthermore, while the embodiments illustrated in FIGS. 8 through 11 are based on the embodiment of FIG. 2 with one or more components of the device of FIG. 2 being placed externally, the configuration of the embodiments shown in FIGS. 8 through 11 may be applied to the embodiments shown in FIGS. 3 through 7.

The spraying composition, which is the material of film formation using the electrostatic spray devices 10 of the foregoing embodiments, may contain (a) a volatile substance and (b) a film-forming polymer.

The volatile substance as component (a) is a substance exhibiting volatility when in the form of liquid. Component (a) is incorporated into the spraying composition with a view to forming a dry coating film through the following mechanism. The spray composition is sufficiently charged in an electric field and ejected from the tip of the nozzle to the skin. As component (a) evaporates, the charge density of the spraying composition increases excessively. Thus, the liquid droplets further reduce in size by Coulomb repulsion, and component (a) further evaporates to form a dry film ultimately. To achieve this purpose, the vapor pressure of the volatile substance is preferably 0.01 to 106.66 kPa, more preferably 0.13 to 66.66 kPa, even more preferably 0.67 to 40.00 kPa, still more preferably 1.33 to 40.00 kPa.

Component (a) may preferably be one or more volatile substances selected from, for example, water, alcohols, and ketones. Suitable alcohols include monohydric acyclic aliphatic alcohols, monohydric cyclic aliphatic alcohols, and monohydric aromatic alcohols. Specific examples of the alcohols include ethanol, isopropyl alcohol, butanol, phenylethyl alcohol, propanol, and pentanol. These alcohols may be used either individually or in combination thereof. Examples of the ketones include acetone, methyl ethyl ketone, and methyl isobutyl ketone. These ketones may be used either individually or in combination thereof.

The volatile substance (a) is preferably one or more selected from ethanol, isopropyl alcohol, butanol, and water, more preferably one or more selected from ethanol and butanol, most preferably ethanol.

The film-forming polymer as component (b) is usually a substance capable of dissolving in the volatile substance (a). As used herein, the expression "capable of dissolving" means being capable of forming a dispersion at 20° C. that is visually uniform, preferably visually transparent or semi-transparent.

The film-forming polymer (b) is selected as appropriate according to the properties of the volatile substance (a). Useful film-forming polymers are roughly divided into water soluble polymers and water insoluble polymers. As used herein, the term "water soluble polymer" denotes a polymer having solubility such that, when a sample polymer weighing 1 g is immersed in 10 g of ion-exchanged water for 24 hours at 23° C. and 1 atm, at least 0.5 g of the immersed polymer dissolves in the ion-exchanged water. As used herein, the term "water insoluble polymer" denotes a polymer having properties such that, when a sample polymer weighing 1 g is immersed in 10 g of ion-exchanged water for 24 hours at 23° C. and 1 atm, more than 0.5 g of the immersed polymer does not dissolve in the ion-exchanged water.

Examples of useful water-soluble, film forming polymers include naturally-occurring polymers, such as mucopolysaccharides, e.g., pullulan, hyaluronic acid, chondroitin sulfate, poly-γ-glutamic acid, modified corn starch, β-glucan, gluco-oligosaccharides, heparin, and keratosulfate, cellulose, pectin, xylan, lignin, glucomannan, polygalacturonic acid, *psyllium* seed gum, tamarind seed gum, gum arabic, tragacanth gum, water soluble soybean polysaccharides, alginic acid, carrageenan, laminaran, agar (agarose), fucoidan, methyl cellulose, hydroxypropyl cellulose, and hydroxypropylmethyl cellulose; and synthetic polymers, such as partially saponified polyvinyl alcohol (PVA) (usable in the absence of a crosslinking agent), low-saponified PVA, polyvinylpyrrolidone (PVP), polyethylene oxide, and sodium polyacrylate. The water soluble polymers recited may be used either individually or in combination of two or more thereof. Preferred of them are pullulan and synthetic polymers, such as partially saponified PVA, low-saponified PVA, polyvinylpyrrolidone, and polyethylene oxide, in the interests of ease of nanofiber production. In using polyethylene oxide as the water soluble polymer, the number average molecular weight of the polyethylene oxide is preferably 50,000 to 3,000,000, more preferably 100,000 to 2,500,000.

Examples of useful water-insoluble, film-forming polymers include completely saponified PVA that can be insolubilized after film formation, partially saponified PVA with a crosslinking agent that can be crosslinked in the presence of a crosslinking agent after film formation, oxazoline-modified silicones, such as a poly(N-propanoylethyleneimine) grafted-dimethyl siloxane/γ-aminopropylmethylsiloxane copolymer, polyvinyl acetal diethylaminoacetate, zein (main component of maize protein), polyesters, polylactic acid (PLA), acrylic resins (e.g., polyacrylonitrile resins and polymethacrylic acid resins), polystyrene resins, polyvinyl butyral resins, polyethylene terephthalate resins, polybutylene terephthalate resins, polyurethane resins, polyamide resins, polyimide resins, and polyamideimide resins. The water insoluble polymers may be used either individually or in combination of two or more thereof. Preferred of them are completely saponified PVA that can be insolubilized after film formation, partially saponified PVA with a crosslinking agent that can be crosslinked in the presence of a crosslinking agent after nanofiber formation, polyvinyl butyral resins, oxazoline-modified silicones, such as γ-aminopropylmethylsiloxane copolymers, water soluble polyesters, and zein.

The content of component (a) in the spraying composition is preferably 50 mass % or higher, more preferably 55 mass % or higher, even more preferably 60 mass % or higher, and preferably 98 mass % or lower, more preferably 96 mass % or lower, even more preferably 94 mass % or lower. The content of component (a) in the spraying composition preferably ranges from 50 to 98 mass %, more preferably 55 to 96 mass %, even more preferably 60 to 94 mass %. The spraying composition containing component (a) in an amount within the above range sufficiently evaporates in electrostatic spraying operation.

The content of component (b) in the spraying composition is preferably 2 mass % or higher, more preferably 4 mass % or higher, even more preferably 6 mass % or higher, and preferably 50 mass % or lower, more preferably 45 mass % or lower, even more preferably 40 mass % or lower. The content of component (b) in the composition preferably ranges from 2 to 50 mass %, more preferably from 4 to 45 mass %, even more preferably from 6 to 40 mass %. The spraying composition containing component (b) in an amount in that range is capable of forming a desired film successfully.

The spraying composition may be composed solely of components (a) and (b) or may further contain other components in addition to components (a) and (b). Examples of other useful components include plasticizers for the film-forming polymers as component (b), coloring pigments, extender pigments, dyes, surfactants, UV protectors, fragrances, repellents, antioxidants, stabilizers, preservatives, and various vitamins. The total content of the other components, if used, in the spraying composition is preferably 0.1 to 30 mass %, more preferably 0.5 to 20 mass %.

The electrostatic spray device of the invention may be used to form a film directly on the bare skin. The film may also be formed on the skin to which cosmetics have already been applied (hereinafter also called "cosmetic-applied area"). That is, a film may be formed as a topcoat on a cosmetic-applied area to cover and protect the applied cosmetic layer. The thus covered cosmetic layer is prevented effectively from staining clothing even if it contacts clothing.

In forming a film onto a cosmetic-applied area using the electrostatic spray device of the invention, it is recommended to form a film over the entire cosmetic-applied area so as to certainly prevent the cosmetic from staining other objects such as clothing that may contact the makeup and to help the cosmetic last long on the skin. Occasionally, a film may be formed only part of the cosmetic-applied area. Otherwise, a film may be formed to straddle a cosmetic-applied area and the bare skin.

The term "cosmetic(s)" as used herein includes makeup cosmetics, UV cosmetics, and topical preparations for providing the preferable skin conditions, such as beauty essence. Examples of makeup cosmetics include base makeup, lip cosmetics, makeup bases, BB creams, and CC creams. Examples of base makeup include foundations, concealers, and face powders. The base makeup products contain particles, such as coloring pigments and extender pigments, and their forms (e.g. liquid, jell, emulsion, or solid) make no essential difference.

The coloring pigments and extender pigments contained in base makeup may be any of those commonly used in cosmetics. Examples of useful pigments include inorganic particles, such as silicic acid, silicic anhydride, magnesium silicate, talc, sericite, mica, kaolin, red iron oxide, clay, bentonite, mica, titanated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine blue, chromium oxide, chromium hydroxide, calamine, carbon black, boron nitride, and composites thereof; organic particles, such as polyamides, nylons, polyesters, polypropylene, polystyrene, polyurethanes, vinyl resins, urea resins, phenol resins, fluororesins, silicon resins, acrylic resins, melamine resins, epoxy resins, polycarbonate resins, divinylbenzene-styrene copolymers, silk powder, cellulose, long chain alkylphosphoric acid metal salts, N-mono(long chain)alkylacyl basic amino acids, and composites thereof; and particulate composites of the organic and inorganic particles recited. The extender pigments and coloring pigments are either colored or non-colored (e.g., white or essentially transparent) and are capable of imparting one or more cosmetic effects or benefits, such as coloration, light diffraction, oil absorption, semi-transparency, opaqueness, gloss, matte appearance, and smoothness.

Considering the effect in preventing applied cosmetics from adhering to clothing, suitable cosmetics are those containing coloring pigments or pearlescent pigments. Examples of such coloring pigments include inorganic pigments, such as titanium oxide, zinc oxide, yellow iron oxide, red iron oxide, black iron oxide, carbon black, ultramarine blue, Prussian blue, blue titanium oxide, black titanium oxide, chromium oxide, chromium hydroxide, and a titanium/titanium oxide sintered product; organic pigments, such as Red No. 201, Red No. 202, Red No. 226, Yellow No. 401, and Blue No. 404; lake pigments, such as Red No. 104, Red. No. 230, Yellow No. 4, Yellow No. 5, and Blue No. 1; and organic pigments coated with polymers, such as a polymethacrylic ester. Examples of the pearlescent pigments include inorganic particles, such as titanated mica, red iron oxide-coated mica, bismuth oxychloride, titanium oxide-coated bismuth oxychloride, iron oxide-coated titanated mica, organic pigment-coated titanated mica, silicic acid/titanium-treated mica, titanium oxide-coated talc, silicon dioxide/red iron oxide-treated aluminum, and titanium oxide-coated glass powder; and flaky aluminum particles coated with an organic resin (e.g., polyethylene terephthalate). The coloring pigments, extender pigments, and pearlescent pigments may be surface-treated with a fluorine-containing compound or a silicone compound to have improved durability against sweat or sebum.

The makeup cosmetics may contain, in addition to the particulate coloring pigment or extender pigment, an oil that is liquid at 25° C. or a wax that is solid at 25° C. The makeup cosmetics may further contain other common ingredients, such as thickening agents, film-forming agents, surfactants, sugars, polyhydric alcohols, water soluble polymers, metallic ion scavengers, lower alcohols, amino acids, organic amines, pH adjustors, skin conditioning agents, vitamins, antioxidants, fragrances, and preservatives, as long as the effects of the invention are not impaired.

The UV cosmetics preferably contain ingredients having UV protective properties, such as UV absorbers and UV scattering agents. The UV absorber is preferably at least one organic UV absorber selected from benzophenone derivatives, such as dihydroxybenzophenone, dihydroxydimethoxybenzophenone, hydroxymethoxybenzophenone sulfonate, and dihydroxydimethoxybenzophenone disulfonate; and methoxycinnamic acid derivatives, such as 2-ethylhexyl methoxycinnamate. More preferred is 2-ethylhexyl methoxycinnamate. Examples of the UV scattering agents include zinc oxide, titanium oxide, and silica, each having an average particle size of 0.1 µm or smaller.

By the use of the electrostatic spray device of the invention, a spraying composition can be attached to the skin in the form of liquid droplets or in the form of fiber. The electrostatic spray device of the invention is advantageous in that a film composed of deposited fiber is successfully formed. In forming a film composed of deposited fiber, the thickness of the fiber in terms of circle equivalent diameter is preferably 10 nm or greater, more preferably 50 nm or greater, preferably 3000 nm or smaller, more preferably 1000 nm or smaller. The thickness of the fiber can be measured by, for example, observing the fiber at a magnification of 10,000 times under a scanning electron microscope (SEM), deleting defects (e.g., lumps of fibers, intersections of fibers, and liquid droplets) from the two-dimensional micrograph, randomly choosing ten fibers, drawing a line perpendicular to the longitudinal direction of each fiber chosen, and directly reading the length of the line segment crossing the fiber.

While the fiber may possibly have an infinite length in principle, it preferably has a length at least 100 times the thickness. In the description, a fiber having a length 100 or more times the thickness is designated a "continuous filament". The film formed by the use of the electrostatic spray device of the invention is preferably a porous discontinuous film made up of deposited continuous filaments. A film having such a porous form is advantageous in that it is an aggregate that can be handled as a single sheet, characteristically very soft, less likely to disintegrate even with a shearing force applied thereto, and highly conformable to the body movement. The porous film also has the advantage of excellent dissipation of sweat from the skin. The porous film also has the advantage of ease of removal. In contrast, a poreless continuous film is not easy to strip off and has so poor sweat dissipation as to cause skin overhydration easily.

The spray composition in the form of fiber (filament) reaches the skin in a charged state. As previously noted, since the skin is also charged, the fiber adheres tightly to the skin by electrostatic force. Because the surface of the skin has a very fine-scale roughness (texture), the adhesion of the film to the skin is ensured by the anchoring effect of such a surface roughness. On completion of electrostatic spraying, the device 10 is turned off. The electric field between the nozzle and the skin thus disappears, and the charges are fixed on the skin surface. Consequently, the adhesion of the film further develops.

While the above description is about a porous film composed of deposited fibers, the film formed by the electrostatic spray device of the invention is not limited to the porous film. The film may be a poreless continuous film or may be a porous film having a form other than deposited fibers, such as a porous film, i.e., a discontinuous film, made by forming a plurality of through-holes in a regular or irregular pattern in a continuous film. As stated earlier, a film of any desired shape can be formed by adjusting the viscosity of the spraying composition, the distance between the nozzle and the skin, and the voltage applied to the nozzle.

To form a film successfully, the distance between the nozzle and the skin is preferably 50 mm to 150 mm, while depending on the voltage applied to the nozzle. The nozzle-to-skin distance may be measured using a commonly employed non-contact sensor.

Irrespective of whether the film formed by electrostatic spraying is porous, the weight of the film is preferably 0.1 g/m$^2$, more preferably 1 g/m$^2$, preferably 30 g/m$^2$ or less, more preferably 20 g/m$^2$ or less. For example, the weight of the film is preferably 0.1 to 30 g/m$^2$, more preferably 1 to 20 g/m$^2$. With that weight, the film exhibits improved adhesion.

While the invention has been described with reference to its preferred embodiments, it should be understood that the invention is not limited thereto. For example, each of the embodiments illustrated in FIGS. 2 through 6 may further include any two or more of the stop function used in the embodiment shown in FIG. 3, the angle measurement unit of the embodiment shown in FIG. 4, the color detection unit of the embodiment shown in FIG. 5, and the smoothness detection unit of the embodiment shown in FIG. 6.

While in the foregoing embodiments, a person who wants to form a film on his or her own skin holds the electrostatic spray device 10 and operates the device to generate an electric field between the nozzle and his or her skin, a person who wants to form a film on his or her own skin does not need to hold the device 10 in his or her own hand as long as an electric field is generated between the nozzle and his or her skin While in the embodiments of FIGS. 2 through 6, the various notification units are each composed of two means, one by lighting a lamp(s), and the other by sound or vibration, the notification unit may have either one of these means, or may have any other additional means, or may have at least one of these means combined with any other means.

The following clauses are disclosed with reference to the foregoing embodiments.

(1) A film forming device for forming a film on the skin by electrostatic spraying, including:

a distance measurement unit for measuring the distance between the skin on which a film is to be formed and the film forming device, a distance decision unit for deciding whether the distance measured by the distance measurement unit is proper for electrostatic spraying, and a distance notification unit for notifying a user of the decision made by the distance decision unit, the film forming device being of hand-held type small enough, and configured, to be held by the user's hand.

(2) The film forming device according to clause (1), further including an auxiliary circuit, wherein the distance measurement unit is electrically connected to the auxiliary circuit, the distance decision unit is incorporated into the auxiliary circuit, and the distance decision unit is equipped with an upper limit input/memory unit and a lower limit input/memory unit.

(3) The film forming device according to clause (2), wherein the distance notification unit has a distance indicator that notifies the user of the distance by lighting a lamp and an alarm that notifies the user of the distance by sound or vibration.

(4) A film forming device for forming a film on the skin by electrostatic spraying, including:

a distance measurement unit for measuring the distance between the skin on which a film is to be formed and the film forming device and a voltage control unit for adjusting the output voltage of a high-voltage supply used to carry out electrostatic spraying in accordance with the distance measured by the distance measurement unit, the film forming device being of hand-held type small enough, and configured, to be held by the user's hand.

(5) The film forming device according to any one of clauses (1) to (4), further including an angle measurement unit for measuring the angle between the electrostatic spray direction and the skin on which the film is to be formed.

(6) The film forming device according to clause (5), wherein the angle measurement unit is composed of three distance measurement units, the three distance measurement units being arranged at the vertices of a regular triangle when viewed from one of the longitudinal ends of the electrostatic spray device.

(7) The film forming device according to any one of clauses (1) to (4), further including a distance notification unit and an angle notification unit.

(8) The film forming device according to clause (7), wherein the angle notification unit has a distance indicator and an alarm, the angle indicator functioning to notify the user of the distance by lighting a lamp, and the alarm functioning to notify the user of the angle by sound or vibration.

(9) The film forming device according to any one of clauses (1) to (8), having a stop function for stopping the electrostatic spraying in the event of a deviation of the distance between the skin on which a film is to be formed and the film forming device from a set range during electrostatic spraying.

(10) The film forming device according to any one of clauses (1) to (9), further including a color detection unit for detecting the color of a film being formed by electrostatic spraying, a color decision unit for deciding whether the color measured by the color detection unit is within a set range, and a color notification unit for notifying the user of the decision made by the color decision unit.

(11) The film forming device according to clause (10), wherein the color notification unit has a color indicator for notifying the user of the color of the film being formed by lighting a lamp and an alarm for notifying the user of the color of the film being formed by sound or vibration.

(12) The film forming device according to any one of clauses (1) to (11), further including a smoothness detection unit for detecting the smoothness of the film being formed by electrostatic spraying, a smoothness decision unit for deciding whether the smoothness of the film being formed detected by the smoothness detection unit is within a set range, and a smoothness notification unit for notifying the user of the decision made by the smoothness decision unit.

(13) The film forming device according to clause (12), wherein the smoothness notification unit has a smoothness indicator for notifying the user of the smoothness of the film being formed by lighting a lamp and an alarm for notifying the user of the smoothness of the film being formed by sound or vibration.

(14) The film forming device according to any one of clauses (1) to (13), being configured to apply a spraying composition to the skin in the form of fiber by electrostatic spraying.

(15) The film forming device according to any one of clauses (1) to (14), further including a housing and a nozzle, the nozzle being disposed with its tip projecting toward the skin along the longitudinal direction of the housing.

(16) The film forming device according to any one of clauses (1) to (15), including a main body, a housing separate from the main body, and a reservoir separate from the main body and configured to contain a spraying composition for electrostatic spraying the reservoir being contained in the housing and connected to the main body via a flexible tube.

(17) The film forming device according to clause (16), further including a feeder for delivering the spraying composition to the main body, the feeder being contained in the housing and connected to the main body via a flexible tube and an electric wire.

(18) The film forming device according to clause 17, wherein the flexible tube and the electric wire are contained in a single flexible tube.

(19) The film forming device according to any one of clauses (16) to (18), further including a low-voltage supply for driving the main body, the low-voltage supply being contained in the housing and connected to the main body via an electric wire.

(20) The film forming device according to clause (19), wherein the flexible tube and the electric wire each connecting the main body and the feeder and the electric wire connecting the main body and the low-voltage supply are contained in a single flexible tube.

(21) The film forming device according to any one of clauses (16) to (20), further including a high-voltage supply for generating a high voltage for conducting electrostatic spraying, the high-voltage supply being contained in the housing and connected to the main body via an electric wire.

(22) The film forming device according to clause (21), wherein the flexible tube and the electric wire each connecting the main body and the feeder, the electric wire connecting the main body and the low-voltage supply, and the electric wire connecting the main body and the high-voltage supply are contained in a single flexible tube.

INDUSTRIAL APPLICABILITY

The film forming device of the invention enables forming a proper electric field between itself and an object on which a film is to be formed thereby to perform electrostatic spraying satisfactorily.

The invention claimed is:

1. A film forming device for forming a film on the skin by electrostatic spraying, wherein said film is formed by drawing a polymer into fibers that form a porous film made up of an aggregation of deposited fibers on the skin, said device comprising:

a distance measurement unit for measuring the distance between the skin on which the film is to be formed and the film forming device, a distance decision unit for deciding whether the distance measured by the distance measurement unit is proper for electrostatic spraying, and a distance notification unit for notifying a user of the decision made by the distance decision unit, the film forming device being configured to apply a spraying composition in the form of fiber to the skin by electrostatic spraying, and the film forming device being of hand-held type small enough, and configured, to be held by the user's hand.

2. A film forming device for forming a film on the skin by electrostatic spraying, wherein said film is formed by drawing a polymer into fibers that form a porous film made up of an aggregation of deposited fibers on the skin, said device comprising:

a distance measurement unit for measuring the distance between the skin on which the film is to be formed and the film forming device, a high-voltage supply for carrying out electrostatic spraying, and a voltage control unit for adjusting the output voltage of the high-voltage supply in accordance with the distance measured by the distance measurement unit, the film forming device being configured to apply a spraying composition in the form of fiber to the skin by electrostatic spraying, and the film forming device being of hand-held type small enough, and configured, to be held by the user's hand.

3. The film forming device according to claim 1, further comprising an angle measurement unit for measuring the angle between the electrostatic spray direction and the skin on which the film is to be formed.

4. The film forming device according to claim 1, having a stop function for stopping the electrostatic spraying in the event of a deviation of the distance between the skin on which a film is being formed and the film forming device from a set range during electrostatic spraying.

5. The film forming device according to claim 1, further comprising a color detection unit for detecting the color of a film being formed by electrostatic spraying,
   a color decision unit for deciding whether the color measured by the color detection unit is within a set range, and
   a color notification unit for notifying the user of the decision made by the color decision unit.

6. The film forming device according to claim 1, further comprising a smoothness detection unit for detecting the smoothness of the film being formed by electrostatic spraying,
   a smoothness decision unit for deciding whether the smoothness of the film being formed detected by the smoothness detection unit is within a set range, and
   a smoothness notification unit for notifying the user of the decision made by the smoothness decision unit.

7. The film forming device according to claim 1, comprising a main body, a housing separate from the main body, and a reservoir separate from the main body and configured to contain a spraying composition for electrostatic spraying,
   the reservoir being contained in the housing and connected to the main body via a flexible tube.

8. The film forming device according to claim 7, further comprising a feeder for delivering the spraying composition to the main body,
   the feeder being contained in the housing and connected to the main body via an electric wire.

9. The film forming device according to claim 7, further comprising a high-voltage supply for generating a high voltage for conducting electrostatic spraying,
   the high-voltage supply being contained in the housing and connected to the main body via an electric wire.

* * * * *